United States Patent
Millard et al.

(10) Patent No.: US 12,419,990 B2
(45) Date of Patent: Sep. 23, 2025

(54) OPHTHALMIC VISCOELASTIC COMPOSITIONS

(71) Applicant: Bausch & Lomb Incorporated, Rochester, NY (US)

(72) Inventors: Kimberly Anne Millard, Rochester, NY (US); Madhu Ayyagari, Rancho Santa Margarita, CA (US); Erning Xia, Penfield, NY (US); Bill Reindel, Webster, NY (US)

(73) Assignee: BAUSCH & LOMB INCORPORATED, Rochester, NY (US)

( * ) Notice: Subject to any disclaimer, the term of this patent is extended or adjusted under 35 U.S.C. 154(b) by 561 days.

(21) Appl. No.: 16/193,537

(22) Filed: Nov. 16, 2018

(65) Prior Publication Data

US 2019/0151500 A1     May 23, 2019

Related U.S. Application Data

(60) Provisional application No. 62/589,866, filed on Nov. 22, 2017.

(51) Int. Cl.
| | |
|---|---|
| *A61K 47/36* | (2006.01) |
| *A61F 9/00* | (2006.01) |
| *A61F 9/007* | (2006.01) |
| *A61K 47/02* | (2006.01) |
| *A61K 47/18* | (2017.01) |
| *A61L 27/02* | (2006.01) |
| *A61L 27/12* | (2006.01) |
| *A61L 27/20* | (2006.01) |
| *A61L 27/36* | (2006.01) |
| *A61L 31/04* | (2006.01) |
| *A61L 31/14* | (2006.01) |

(52) U.S. Cl.
CPC ............ *A61L 27/20* (2013.01); *A61F 9/0017* (2013.01); *A61F 9/00754* (2013.01); *A61L 27/025* (2013.01); *A61L 27/12* (2013.01); *A61L 27/3637* (2013.01); *A61L 31/042* (2013.01); *A61L 31/143* (2013.01); *A61K 47/02* (2013.01); *A61K 47/18* (2013.01); *A61K 47/36* (2013.01); *A61L 2400/06* (2013.01); *A61L 2400/16* (2013.01); *A61L 2430/16* (2013.01)

(58) Field of Classification Search
None
See application file for complete search history.

(56) References Cited

U.S. PATENT DOCUMENTS

| | | | |
|---|---|---|---|
| 3,589,363 A | 6/1971 | Banko et al. | |
| 3,693,613 A | 9/1972 | Kelman | |
| 5,718,676 A | 2/1998 | Barrett | |
| 5,853,767 A * | 12/1998 | Melman | A61K 33/22 514/557 |
| 5,880,107 A | 3/1999 | Buenter | |
| 6,517,933 B1 | 2/2003 | Soane et al. | |
| 6,558,419 B1 | 5/2003 | Pham et al. | |
| 10,195,225 B2 | 2/2019 | Tezel et al. | |
| 10,413,567 B2 * | 9/2019 | Ranatunga | A61K 31/724 |
| 2003/0044468 A1 | 3/2003 | Cellesi et al. | |
| 2003/0133905 A1 * | 7/2003 | Hu | A61L 12/14 424/78.31 |
| 2004/0167480 A1 | 8/2004 | Bos | |
| 2005/0234012 A1 | 10/2005 | Jafari et al. | |
| 2006/0100173 A1 * | 5/2006 | Powell | A61L 12/141 514/54 |
| 2006/0121016 A1 * | 6/2006 | Lee | A61K 31/198 424/94.4 |
| 2007/0243180 A1 * | 10/2007 | Tanaka | A61P 39/06 424/94.1 |
| 2008/0171393 A1 | 7/2008 | Lu et al. | |
| 2010/0036387 A1 * | 2/2010 | Bucolo | A61L 31/042 606/107 |
| 2012/0108672 A1 | 5/2012 | Tsutsui et al. | |
| 2013/0310732 A1 | 11/2013 | Foschini et al. | |
| 2013/0338240 A1 * | 12/2013 | Findl | A61K 9/08 514/781 |
| 2016/0296666 A1 * | 10/2016 | Shachaf | A61L 27/18 |
| 2017/0087177 A1 | 3/2017 | Belmonte | |
| 2017/0312306 A1 | 11/2017 | Ranatunga et al. | |

FOREIGN PATENT DOCUMENTS

| | | |
|---|---|---|
| AU | 2018372826 | 9/2023 |
| CN | 101574537 B | 11/2009 |
| CN | 102225220 A | 10/2011 |
| CN | 102481268 A | 5/2012 |
| CN | 105164204 A | 12/2015 |
| CN | 105214093 A * | 1/2016 |
| EP | 0781547 B1 | 4/2002 |
| JP | 2002332248 A | 11/2002 |
| KR | 20060131938 A | 12/2006 |
| KR | 10-2020-7017563 | 6/2023 |
| WO | 2005097225 A1 | 10/2005 |

(Continued)

OTHER PUBLICATIONS

Deckner, Hyaluronic Acid: A Ubiquitous Biopolymer, Jan. 22, 2016, Prospector Knowledge Center, printed from https://knowledge.ulprospector.com/3691/pcc-hyaluronic-acid/, 4 pages.*

Flinders University, Appendix 1 Solutions—Tris-Phosphate Buffer Saline (TPBS) and 0.4M phosphate buffer, Nov. 28, 2015, Google date sheet, printed from https://flex.flinders.edu.au/file/76d259ae-f350-4e10-b898-db888d8b83c6/1/Thesis-David-2009-08Appendix.pdf, 6 pages.*

(Continued)

*Primary Examiner* — Gigi G Huang
(74) *Attorney, Agent, or Firm* — Michael E. Carmen; John E. Thomas

(57) ABSTRACT

A viscoelastic composition is disclosed which comprises (a) tris(hydroxymethyl)aminomethane or a salt thereof; (b) a phosphate buffer agent; and (c) a viscoelastic agent having an average molecular weight of about 100 to about 5,000,000.

29 Claims, 1 Drawing Sheet

(56) References Cited

FOREIGN PATENT DOCUMENTS

| WO | 2005097226 A1 | 10/2005 |
|---|---|---|
| WO | 2006039458 A1 | 4/2016 |
| WO | 2017044659 A1 | 3/2017 |
| WO | 2017053339 A1 | 3/2017 |
| WO | PCT/US2018/061526 | 2/2019 |

OTHER PUBLICATIONS

Sek, Breaking old habits: Moving away from commonly used buffers in pharmaceuticals, European Pharmaceutical Review, Issue 3 2012, printed from https://www.europeanpharmaceuticalreview.com/article/13699/breaking-old-habits-moving-away-from-commonly-used-buffers-in-pharmaceuticals/, 12 pages.*

Ball, A. et al., "On the molecular weight distribution of dextran T-500", Gums and Stabilisers for the Food Industry, 1990, vol. 5, pp. 447-450.

\* cited by examiner

OPHTHALMIC VISCOELASTIC COMPOSITIONS

BACKGROUND OF THE INVENTION

The present invention generally relates to ophthalmic viscoelastic compositions and a method for conducting ocular surgery in an eye using the ophthalmic viscoelastic composition.

In the past decade, advances in the technology of eye surgery have made surgical treatment of eye disease and deformities attractive to alternative therapies. Cataract removal is one of the more common surgical procedures. Cataracts are opacities of the ocular lens, which generally arise in the elderly. Typically, cataract surgery involves first removing the cataractous lens from the capsular bag and then replacing the cataractous lens with a synthetic intraocular lens. Presently, this procedure involves making an incision through the sclera and into the anterior chamber of the patient's eye. Another incision is then made into the capsular bag. The cataractous lens is fractured in the capsular bag by a procedure such as phacoemulsification and then removed from the capsular bag by a procedure such as aspiration. Thereafter an intraocular lens is inserted into the capsular bag and deployed therein.

The overall procedure is potentially traumatic to the capsular bag and the tissue surrounding the anterior chamber. It is advantageous to reduce the amount of trauma to any living tissue in the patient's eye during a surgical procedure. In particular, lens endothelial cells in the capsular bag are sensitive to damage. Damage to the lens endothelial cells is often permanent. Serious damage can cause loss of eyesight and failure of the surgical procedure.

A problem associated with the process of phacoemulsification is the production of free radicals and/or oxidants. Free radicals and/or oxidants are unstable and react somewhat indiscriminately with biological molecules in tissue. For example, a free radical and/or oxidant that are produced in phacoemulsification can damage proteins, cell walls or even the DNA of a cell. It is therefore advantageous to reduce the damage caused by these free radicals and/or highly reactive ions.

In general, when conducting ocular surgery in a human eye, a viscoelastic composition is injected in the anterior chamber of the eye and the capsular bag during surgery to protect the tissue from physical trauma. The viscoelastic composition provides a physical barrier or cushion between the instruments and the tissue. Furthermore, the viscoelastic composition assists in maintaining the shape of a cavity during operation including the anterior chamber and capsular bag.

Typically, the viscoelastic compositions are stored in a cool environment, e.g., a refrigerator, prior to use. When conducting surgery, the viscoelastic compositions are first removed from the cool environment and allowed to warm to room temperature. The viscoelastic compositions however must meet the required specifications in order to be used. One such required specification is the pH of the composition.

One example of a viscoelastic composition is disclosed in U.S. Patent Application Publication No. 2010/036387 which contains hyaluronic acid and/or salts thereof, hydroxypropyl methylcellulose, tris(hydroxymethyl)aminomethane and a hexahydric alcohol. However, a problem associated with the use of this composition is that the pH of the viscoelastic composition is temperature dependent. When stored in a cool environment, the viscoelastic composition does not meet the required pH specification. Accordingly, the viscoelastic composition must be brought to room temperature in order to be used. However, this is not typically the case when conducting ocular surgery.

Accordingly, it would be desirable to provide an improved viscoelastic composition which has a pH that meets the required pH specification in both cool temperatures during storage and at room temperature for use.

SUMMARY OF THE INVENTION

In accordance with one embodiment of the present invention, there is provided a viscoelastic composition comprising:
(a) tris(hydroxymethyl)aminomethane or a salt thereof;
(b) a phosphate buffer agent; and
(c) a viscoelastic agent having an average molecular weight of about 100 to about 5,000,000.

In accordance with a second embodiment of the present invention, there is provided a method for conducting ocular surgery in an eye having an anterior chamber, a posterior chamber and a capsular bag located within the posterior chamber, the method comprising, after the eye has been surgically opened:
filling the anterior chamber with a first viscoelastic composition comprising (i) tris(hydroxymethyl)aminomethane or a salt thereof; (ii) a phosphate buffer agent; and (iii) a viscoelastic agent having an average molecular weight of about 100 to about 1,900,000.

In accordance with a third embodiment of the present invention, there is provided a method for conducting ocular surgery in an eye having an anterior chamber, a posterior chamber and a capsular bag located within the posterior chamber, the method comprising:
filling the capsular bag with a viscoelastic composition comprising (i) tris(hydroxymethyl)aminomethane or a salt thereof; (ii) a phosphate buffer agent; and (iii) a viscoelastic agent having an average molecular weight of about 2,000,000 to about 5,000,000, prior to implantation of an intraocular lens in the capsular bag.

In accordance with a fourth embodiment of the present invention, there is provided a method for conducting ocular surgery in an eye having an anterior chamber, a posterior chamber and a capsular bag located within the posterior chamber, the method comprising
(a) surgically opening the eye;
(b) filling the anterior chamber with a first viscoelastic composition comprising (i) tris(hydroxymethyl)aminomethane or a salt thereof; (ii) a phosphate buffer agent; and (iii) a viscoelastic agent having an average molecular weight about 100 to about 1,000,000;
(c) performing a capsulotomy; removing any cataractous tissue;
(d) filling the capsular bag with a second viscoelastic composition comprising (i) tris(hydroxymethyl)aminomethane or a salt thereof; (ii) a phosphate buffer agent; and (iii) a viscoelastic agent having an average molecular weight of about 2,000,000 to about 5,000,000; and
(e) implanting an intraocular lens in the capsular bag.

The present invention is based on the surprising discovery that the pH of the viscoelastic composition described herein is not temperature dependent. Accordingly, the viscoelastic composition of the present invention has a pH that is comparable at both storage temperature and the temperature used in ocular surgery, i.e., room temperature.

DETAILED DESCRIPTION OF THE PREFERRED EMBODIMENTS

Figure 1A:
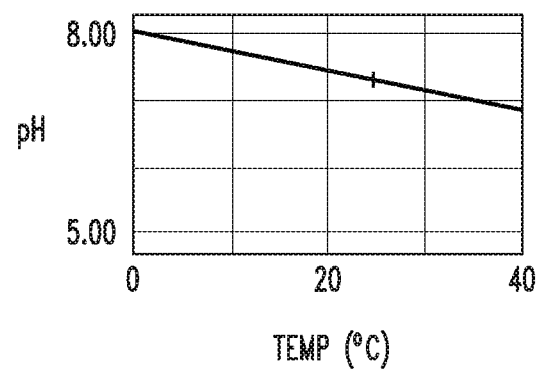
FIGS. 1A and 1B schematically illustrate the predicted pH for a tris buffer (FIG. 1A) versus a dual buffer system as employed in a viscoelastic composition of this invention (FIG. 1B) over the temperature range between storage temperature and ambient temperature.

The present invention is directed to a viscoelastic composition. In general, a viscoelastic composition according to the present invention comprises (a) tris(hydroxymethyl) aminomethane or a salt thereof; (b) a phosphate buffer agent; and (c) a viscoelastic agent having an average molecular weight about 100 to about 5,000,000.

The first component of the viscoelastic composition is tris(hydroxymethyl)aminomethane (2-amino-2-(hydroxymethyl)propane-1,3-diol), (also known as tromethamine, and commonly referred to as tris, tris buffer or tris base) or a salt thereof. In one preferred embodiment, the first component is tris(hydroxymethyl)aminomethane in the base form.

In one embodiment, the tris(hydroxymethyl)aminomethane or a salt thereof is present in the viscoelastic composition according to the present invention in an amount ranging from about 0.001 to about 1 wt. %, based on the total weight of the viscoelastic composition. In another embodiment, the tris(hydroxymethyl)aminomethane or salt thereof is present in the viscoelastic composition according to the present invention in an amount ranging from about 0.05 to about 1 wt. %, based on the total weight of the viscoelastic composition.

A suitable phosphate buffer agent can be any known phosphate buffer agent for use in a viscoelastic composition. In one embodiment, the phosphate buffer agent comprises one or more of sodium hydrogen phosphate monobasic, sodium hydrogen phosphate dibasic, potassium hydrogen phosphate monobasic and potassium hydrogen phosphate dibasic.

In one embodiment, the phosphate buffer agent is present in the viscoelastic composition according to the present invention in an amount ranging from about 0.001 to about 2 wt. %, based on the total weight of the viscoelastic composition. In another embodiment, the phosphate buffer agent is present in the viscoelastic composition according to the present invention in an amount ranging from about 1 to about 2 wt. %, based on the total weight of the viscoelastic composition.

In general, a suitable viscoelastic agent for use in the viscoelastic composition according to the present invention is a viscoelastic agent having an average molecular weight of about 100 to about 5,000,000. The average molecular weight of the viscoelastic agent is determined by gel permeation chromatography (GPC) using chromatography size exclusion. Typically, there are two general classes of viscoelastic compositions. A dispersive viscoelastic composition has properties that disperse or coat the tissue well and adhere well to the tissue. A dispersive viscoelastic composition (also known as an "adhesive viscoelastic composition") typically contains a viscoelastic agent of a low molecular weight. A cohesive viscoelastic composition is better at maintaining the space in a cavity in human tissue and is less likely to leak from the cavity under low or zero shear conditions. Typically, a cohesive viscoelastic composition contains a viscoelastic agent of a high molecular weight.

Accordingly, as one skilled in the art will readily appreciate, the suitable viscoelastic agent will depend on whether it is being used in a viscoelastic composition for Stage 1 (i.e., dispersive viscoelastic composition) or Stage 2 (i.e., cohesive viscoelastic composition) of a cataract procedure. Thus, the suitable viscoelastic agent chosen for Stage 1 or Stage 2 will depend on the physical and chemical characteristics of each agent or combination, including, for example, their molecular weight, viscosity, pseudoplasticity, elasticity, rigidity, coatability, cohesiveness, and molecular charge, and the agent's concentration in a product.

In one embodiment, a viscoelastic agent for the dispersive viscoelastic composition of Stage 1 will have an average molecular weight of about 100 to about 1,900,000. In another embodiment, a viscoelastic agent for the dispersive viscoelastic composition of Stage 1 will have an average molecular weight of about 500,000 to about 1,000,000.

In one embodiment, a viscoelastic agent for the cohesive viscoelastic composition of Stage 2 will have an average molecular weight of about 2,000,000 to about 5,000,000. In another embodiment, a viscoelastic agent for the cohesive viscoelastic composition of Stage 2 will have a molecular weight of about 2,000,000 to about 3,000,000.

In one embodiment, a viscoelastic agent for use in the viscoelastic composition according to the present invention comprises a polysaccharide. In one embodiment, a polysaccharide comprises an anionic polysaccharide. Suitable anionic polysaccharides include, for example, hyaluronic acid or a salt thereof, e.g., sodium hyaluronate or potassium hyaluronate, chondroitin sulfate, chitosan, aloe vera, and carboxymethylcellulose. In one embodiment, a polysaccharide comprises a non-ionic polysaccharide. Suitable non-ionic polysaccharides include, for example, hemicellulose, hydroxypropyl methyl cellulose, methylcellulose, and ethylcellulose.

In one embodiment, a viscoelastic agent for use in the viscoelastic composition according to the present invention comprises hyaluronic acid, sodium hyaluronate or potassium hyaluronate.

As one skilled in the art would recognize, the viscosity of the viscoelastic composition according to the present invention is dependent on the amount and the molecular weight of the viscoelastic agent. Accordingly, in one embodiment, a viscoelastic agent can be present in the viscoelastic composition according to the present invention in an amount ranging from about 0.001 to about 10 wt. %, based on the total weight of the viscoelastic composition. In one embodiment, a viscoelastic agent can be present in the viscoelastic composition according to the present invention in an amount ranging from about 0.5 to about 5 wt. %, based on the total weight of the viscoelastic composition.

The viscoelastic compositions according to the present invention can contain one or more additional additives as may be necessary. Suitable one or more additional additives include, for example, an antioxidant, a non-ionic surfactant, an osmolyte and mixtures thereof. As one skilled in the art will recognize, one additive may be multifunctional. For example, an additive that functions as an antioxidant, may also function as an osmolyte.

In one embodiment, an antioxidant is present in the viscoelastic composition according to the present invention in an amount ranging from about 0.001 to about 5 wt. %, based on the total weight of the viscoelastic composition.

In one embodiment, a non-ionic surfactant is present in the viscoelastic composition according to the present invention in an amount ranging from about 0.001 to about 10 wt. %, based on the total weight of the viscoelastic composition.

In one embodiment, an osmolyte is present in the viscoelastic composition according to the present invention in an amount ranging from about 0.01 to about 10 wt. %, based on the total weight of the viscoelastic composition.

In one embodiment, the viscoelastic composition according to the present invention can further include one or more additives such as, for example, L-Carnitine, erythritol, vitamin E TPGS (tocopheryl polyethylene glycol succinate), and the like.

In one embodiment, the viscoelastic composition according to the present invention can further include one or more additives such as, for example, one or more end terminal functionalized surfactants. A suitable end terminal functionalized surfactant includes, by way of example, one or more end terminal functionalized polyethers. Useful polyethers to be end terminal functionalized comprise one or more chains or polymeric components which have one or more (—O—R—) repeats units wherein R is an alkylene or arylene group having 2 to about 6 carbon atoms. The polyethers may be derived from block copolymers formed from different ratio components of ethylene oxide (EO) and propylene oxide (PO). Such polyethers and their respective component segments may include different attached hydrophobic and hydrophilic chemical functional group moieties and segments.

A representative example of a suitable polyether which can be end terminal functionalized is a poloxamer block copolymer. One specific class of poloxamer block copolymers are those available under the trademark Pluronic (BASF Wyandotte Corp., Wyandotte, Mich.). Poloxamers include Pluronics and reverse Pluronics. Pluronics are a series of ABA block copolymers composed of polyethylene oxide)-poly(propylene oxide)-poly(ethylene oxide) blocks as generally represented in Formula VII:

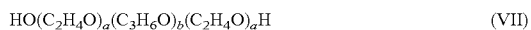

HO(C₂H₄O)ₐ(C₃H₆O)ᵦ(C₂H₄O)ₐH    (VII)

wherein a is independently at least 1 and b is at least 1.

Reverse Pluronics are a series of BAB block copolymers, respectively composed of poly(propylene oxide)-poly(ethylene oxide)-poly(propylene oxide) blocks as generally represented in Formula VIII:

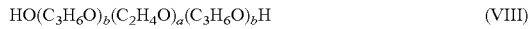

HO(C₃H₆O)ᵦ(C₂H₄O)ₐ(C₃H₆O)ᵦH    (VIII)

wherein a is at least 1 and b is independently at least 1. The polyethylene oxide), PEO, blocks are hydrophilic, whereas the poly(propylene oxide), PPO, blocks are hydrophobic in nature. The poloxamers in each series have varying ratios of PEO and PPO which ultimately determines the hydrophilic-lipophilic balance (HLB) of the material, i.e., the varying HLB values are based upon the varying values of a and b, a representing the number of hydrophilic polyethylene oxide) units (PEO) being present in the molecule and b representing the number of hydrophobic poly(propylene oxide) units (PPO) being present in the molecule.

Poloxamers and reverse poloxamers have terminal hydroxyl groups that can be terminal functionalized, An example of a terminal functionalized poloxamer and as discussed hereinbelow is poloxamer dimethacrylate (e.g., Pluronic® F127 dimethacrylate) as disclosed in U.S. Patent Application Publication No. 2003/0044468. Other examples include glycidyl-terminated copolymers of polyethylene glycol and polypropylene glycol as disclosed in U.S. Pat. No. 6,517,933.

Another example of a suitable polyether which can be end terminal functionalized is a poloxamine block copolymer. While the poloxamers and reverse poloxamers are considered to be difunctional molecules (based on the terminal hydroxyl groups), the poloxamines are in a tetrafunctional form, i.e., the molecules are tetrafunctional block copolymers terminating in primary hydroxyl groups and linked by a central diamine, One specific class of poloxamine block copolymers are those available under the trademark Tetronic (BASF). Poloxamines include Tetronic and reverse Tetronics. Poloxamines have the following general structure of Formula IX:

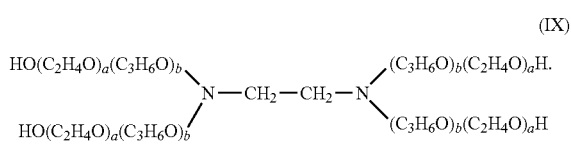

(IX)

wherein a is independently at least 1 and b is independently at least 1.

The poloxamer and/or poloxamine is functionalized to provide the desired reactivity at the end terminal of the molecule. The functionality can be varied and is determined based upon the intended use of the functionalized PEO- and PPO-containing block copolymers. That is, the PEO- and PPO-containing block copolymers are reacted to provide end terminal functionality that is complementary with the intended device forming monomeric mixture. The term block copolymer as used herein shall be understood to mean a poloxamer and/or poloxamine as having two or more blocks in their polymeric backbone(s).

In one embodiment, the viscoelastic composition according to the present invention can further include one or more additives such as, for example, a poloxamer di(meth)acrylate, a reverse poloxamer di(meth)acrylate, a poloxamine di(meth)acrylate, a reverse poloxamine di(meth)acrylate Mirj and Birj.

In one embodiment, the viscoelastic composition according to the present invention can further include one or more additives such as, for example, NaCl, KCl; amino taurine, glycine, diglycine, alanine; mannitol, sorbitol and propylene glycol.

The viscoelastic composition according to the present invention has one or more properties including but not limited to osmolality, and pH, zero-shear viscosity and apparent viscosity measured at 1 rpm. In one embodiment, the osmolality of the viscoelastic composition is a minimum of about 200 mOsmol/Kg and a maximum of about 400 mOsmol/Kg. In one embodiment, the osmolality of the viscoelastic composition is a minimum of about 220 mOsmol/Kg, or about 260 mOsmol/Kg, or about 280 mOsmol/Kg, or about 300 mOsmol/Kg or about 320 mOsmol/Kg and a maximum of about 400 mOsmol/Kg, or about 380 mOsmol/Kg, or about 360 mOsmol/Kg or about 340 mOsmol/Kg.

In one embodiment, the pH of the viscoelastic composition is a minimum of about 5 and a maximum of about 8. In one embodiment, the of the viscoelastic composition can range from about 6.5 to about 7.8. In one embodiment, the pH of the viscoelastic composition is a minimum of about 5.5, or about 6 or about 6.5 and a maximum of about 7.8, or about 7.2 or about 7.

In one embodiment, the low-shear viscosity (cPs shear rate 0.01 sec⁻¹ at 25° C.) of the dispersive viscoelastic composition can range from about 20,000 centipoise (cPs) to about 80,000 cPs. Generally, the low-shear viscosity of the dispersive viscoelastic composition can be at a minimum of about 20,000 cPs, or about 30,000 cPs or about 40,000 cPs and a maximum of about 80,000 cPs or about 70,000 cPs or about 60,000 cPs.

In one embodiment, the apparent viscosity (cPs shear rate 1 sec$^{-1}$ at 25° C.) of the dispersive viscoelastic composition can range from about 15,000 centipoise (cPs) to about 75,000 cPs. Generally, the apparent viscosity of the dispersive viscoelastic composition can be at a minimum of about 15,000 cPs, or about 25,000 cPs or about 35,000 cPs and a maximum of about 75,000 cPs or about 65,000 cPs or about 55,000 cPs.

In one embodiment, the low-shear viscosity (cPs shear rate 0.01 sec$^{-1}$ at 25° C.) of the cohesive viscoelastic composition can range from about 75,000 centipoise (cPs) to about 475,000 cPs. Generally, the low-shear viscosity of the viscoelastic composition can be at a minimum of about 75,000 cPs, or about 125,000 cPs or about 175,000 cPs and a maximum of about 475,000 cPs or about 425,000 cPs or about 375,000 cPs.

In one embodiment, the apparent viscosity (cPs shear rate 1 sec$^{-1}$ at 25° C.) of the viscoelastic composition can range from about 10,000 centipoise (cPs) to about 90,000 cPs. Generally, the apparent viscosity of the viscoelastic composition can be at a minimum of about 10,000 cPs, or about 20,000 cPs or about 30,000 cPs and a maximum of about 90,000 cPs or about 80,000 cPs or about 70,000 cPs.

In one embodiment, a method for conducting ocular surgery in an eye having an anterior chamber, a posterior chamber and a capsular bag located within the posterior chamber is provided, the method comprising, after the eye has been surgically opened:

filling the anterior chamber with a first viscoelastic composition comprising (i) tris(hydroxymethyl)aminomethane or a salt thereof; (ii) a phosphate buffer agent; and (iii) a viscoelastic agent having an average molecular weight of about 100 to about 1,900,000.

The amounts and components of the first viscoelastic composition can be any of those discussed above. The method can further include one or more of the following steps:

performing a capsulotomy;
removing any cataractous tissue;
filling the capsular bag with a second viscoelastic composition; and
implanting an intraocular lens in the capsular bag.

The second viscoelastic composition can be any viscoelastic composition known to fill the capsular bag. In one embodiment, the second viscoelastic composition includes (i) tris(hydroxymethyl)aminomethane or a salt thereof; (ii) a phosphate buffer agent; and (iii) a viscoelastic agent having an average molecular weight of about 2,000,000 to about 5,000,000. The amounts and components of the second viscoelastic composition can be any of those discussed above.

In another embodiment, a method for conducting ocular surgery in an eye having an anterior chamber, a posterior chamber and a capsular bag located within the posterior chamber is provided, the method comprising:

filling the capsular bag with a viscoelastic composition comprising (i) tris(hydroxymethyl)aminomethane or a salt thereof; (ii) a phosphate buffer agent; and (iii) a viscoelastic agent having an average molecular weight of about 2,000,000 to about 5,000,000, prior to implantation of an intraocular lens in the capsular bag. The amounts and components of the viscoelastic composition can be any of those discussed above. The method can further include one or more of the following steps prior to filling the capsular bag:

surgically opening the eye;
filling the anterior chamber with another viscoelastic composition; and
performing a capsulotomy; and removing any cataractous tissue:

The other viscoelastic composition can be any viscoelastic composition known for filling the anterior chamber. In one embodiment, the amounts and components of the other viscoelastic composition can be any of those discussed above for the viscoelastic composition described herein.

Examples of procedures for removing a lens from a patient's eye include, but are not limited to, U.S. Pat. No. 3,589,363 (cataract surgery), U.S. Pat. No. 3,693,613 (phacoemulsification) and U.S. Pat. No. 5,718,676 (process using micro flow needle), which are all incorporated herein by reference in their entirety. The process generally includes providing a passage through a sclera or cornea into an anterior chamber of the eye. The process involves making a small incision into the sclera or cornea. Alternatively or additionally, a cannula or trochar is used to create a passage through the sclera or cornea. In general, the incision or passage is as small as possible, e.g., smaller than about 5 mm, or about 4 mm or about 3 mm. Thereafter, the aqueous humor is withdrawn or otherwise removed from the anterior chamber of the eye.

According to one embodiment, there is a package for a viscoelastic composition according to the present invention that includes a delivery device. The device delivers a viscoelastic composition into the anterior chamber of a patient's eye. The device includes a syringe that contains a viscoelastic composition according to the present invention. The syringe further comprises an outlet port and, optionally, a cannula configured to sealably connect to the outlet port. The cannula has a maximum inner diameter of about 2 mm. Typically, the maximum inner diameter is about 1.8 mm, or about 1.5 mm or about 1 mm. Generally, the minimum inner diameter is about 0.8 min, or about 0.6 mm or about 0.4 mm.

In one embodiment, the viscoelastic composition requires a maximum force of 30 N to pass through a stainless steel cannula having a length of 2.2 cm and an inner diameter of 0.5 mm at a delivery rate of 0.02 ml/sec. In one embodiment, the viscoelastic composition requires a maximum force of about 27 N, about 25 N, about 20 N or about 18 N to pass through a stainless steel cannula having a length of 2.2 cm and an inner diameter of 0.5 mm at a delivery rate of 0.02 ml/sec.

Once the viscoelastic composition is inserted into the anterior chamber the corneal lens is removed. The technique for removing the lens includes performing a capsulorhexis incision and breaking down the lens into smaller pieces through phacoemulsification or other known techniques. Thereafter, the pieces are removed by, for example, aspiration.

The viscoelastic composition is inserted into the capsular bag for space maintenance purposes. Moreover, the viscoelastic composition coats the capsular bag and protects it for additional steps in the surgical procedure. According to one embodiment, the intraocular lens is inserted into the capsular bag. Typically, there is a method of inserting an intraocular lens into a capsular bag of an eye. The method comprises providing a lens insertion device comprising a loadable chamber configured to receive the intraocular lens, a tapered conduit having a first end connected to the loadable chamber and a second end. The second end is configured to penetrate through the passage in the corneal lens and into the capsular bag. An example of a lens insertion device is found in U.S. Pat. No. 6,558,419, which is incorporated herein by reference in its entirety. The lens insertion device is further configured with a slidable actuator. The slidable actuator of one embodiment is configured to actuate the intraocular lens through the conduit past the second end. Typically, the second end of the tapered conduit has an inner diameter that is a maximum of about 5 mm. In one embodiment, the second end of the tapered conduit has an inner diameter that is a maximum of about 4 mm about 3.5 mm, about 3 mm or about 2.8 min. In one embodiment, a maximum force of about 30 N is required to deliver the intraocular lens through the cannula. In one embodiment, a maximum force of about 27 N, about 25 N, about 20 N or about 18 N is required to deliver the intraocular lens through the cannula.

The following examples are provided to enable one skilled in the art to practice the invention and are merely illustrative of the invention. The examples should not be read as limiting the scope of the invention as defined in the claims.

Examples 1 and 2 and Comparative Examples A and B

A viscoelastic composition was made by mixing the following components in the respective amounts listed in Table 1. Example 1 and Comparative Example A are a dispersive viscoelastic composition and Example 2 and Comparative Example B are a cohesive viscoelastic composition.

TABLE 1

| Component | Dispersive (% W/V) | | Cohesive (% W/V) | |
| --- | --- | --- | --- | --- |
| | Example 1 | Comp. Ex. A | Example 2 | Comp. Ex. B |
| Tris (HCl) | NA | 0.530 | NA | 0.530 |
| Tris (Base) | 0.101 | 0.080 | 0.101 | 0.080 |
| Sodium Phosphate, monobasic, monohydrate | 0.138 | NA | 0.138 | NA |
| Sodium Chloride | 0.053 | 0.053 | 0.152 | 0.152 |
| Sorbitol | 4.00 | 4.00 | 4.00 | 4.00 |
| Sodium HA[1] (800K) | 2.00 | 2.00 | NA | NA |
| Sodium HA[2] (1200K) | NA | NA | 2.00 | 2.00 |
| USP H$_2$O | QS to 100 ml | QS to 100 ml | QS to 100 ml | QS to 100 ml |
| Samples were stored at both 4° C. and 22° C. for overnight. The pH assay was performed and recorded below | | | | |
| pH at 22° C. | 7.28 | 7.44 | 7.26 | 7.43 |
| pH at 4° C. | 7.35 | 8.53 | 7.39 | 8.05 |

[1]The average molecular weight of the sodium hyaluronate was 800,000.
[2]The average molecular weight of the sodium hyaluronate was 1,200,000.

As can be seen from Table 1, the pH of the dispersive and cohesive viscoelastic compositions of Examples 1 and 2, respectively, were consistent at both 22° C. and 4° C. as compared to the pH of the dispersive and cohesive viscoelastic compositions of Comparative Examples A and B, respectively, which was significantly different at the two different temperatures. Thus, if the dispersive viscoelastic composition of Example 1 and the cohesive viscoelastic composition of Example 2 are not used as directed, they will have the pH necessary for use at room temperature. Accordingly, a further benefit of the viscoelastic composition according to the present invention, and as exemplified in Examples 1 and 2, is that the formulator can formulate the viscoelastic composition within the scope of the present invention without concern for pH variation at either storage temperature or the intended use at room temperature.

Thus, the dual buffer system as employed in a viscoelastic composition of this invention advantageously allows the formulator to formulate the viscoelastic composition without concern for pH variation at either storage temperature or the intended use at room temperature. This can be further seen in FIGS. 1A and 1B which schematically illustrate the predicted pH using a commercially available software Buffer Maker.exe for a tris buffer (FIG. 1A) versus a dual buffer system as employed in a viscoelastic composition of this invention (FIG. 1B) over the temperature range between storage temperature and ambient temperature. The predicted pH for the tris buffer versus the dual buffer system was based on a 20 mM tris buffer formulation versus an 18.3 mM tris/phosphate buffer formulation as set forth below in Table 2.

TABLE 2

| 20 mM Tris Buffer | 18.3 mM Tris/Phosphate Buffer |
| --- | --- |
| 2.37 mg/mL Tris Base | 1.01 mg/mL Tris Base (8.33 mM) |
| 1N HCL to pH 7.3 (~17 mL) | 1.383 mg/mL Sodium Phosphate Monobasic, monohydrate |
| 40 mg/mL Sorbitol | 40 mg/mL Sorbitol |
| — | 1.70 mg/mL Sodium Chloride |
| pH = 7.3 | pH = 7.31 |
| Ionic Strength = 0.017 | Ionic Strength = 0.06 |

Figure 1B:
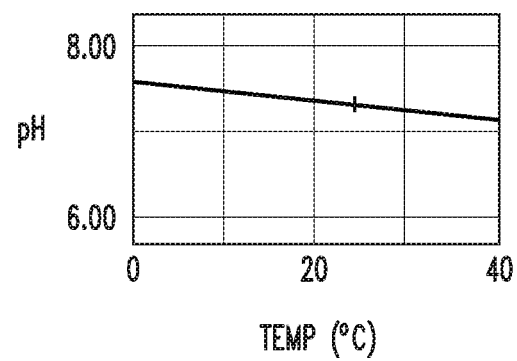

As can be seen in FIG. 1A, the tris buffer was unable to provide a comparable predicted pH from 0° C. to 40° C. However, as shown in FIG. 1B, the duel buffer system was able to provide a comparable predicted pH from 0° C. to 40° C.

Example 3

A viscoelastic composition is made by mixing the following components in the respective amounts listed in Table 3.

TABLE 3

| Component | % W/V |
| --- | --- |
| Tris | 0.1-0.5 |
| Sodium Phosphate, monobasic, monohydrate | 0.1-0.5 |
| Potassium Chloride | 0.01-0.5 |
| Sorbitol | 4.0 |
| HA | 1.5 |

Example 4

A viscoelastic composition is made by mixing the following components in the respective amounts listed in Table 4.

TABLE 4

| Component | % W/V |
| --- | --- |
| Tris | 0.1-0.5 |
| Sodium Phosphate, monobasic, monohydrate | 0.1-0.5 |
| Potassium Chloride | 0.01-0.5 |

TABLE 4-continued

| Component | % W/V |
|---|---|
| Sorbitol | 4.0 |
| L-Carnitine | 0.1 |
| HA | 1.5 |
| HPMC | 0.5 |

Example 5

A viscoelastic composition is made by mixing the following components in the respective amounts listed in Table 5 at amounts per weight.

TABLE 5

| Component | % W/V |
|---|---|
| Tris | 0.1-0.5 |
| Sodium Phosphate, monobasic, monohydrate | 0.1-0.5 |
| Potassium Chloride | 0.01-0.5 |
| Sorbitol | 4.0 |
| L-Carnitine | 0.1 |
| HA | 1.5 |
| Chondroitin sulfate | 0.5 |

Example 6

A viscoelastic composition is made by mixing the following components in the respective amounts listed in Table 6 at amounts per weight.

TABLE 6

| Component | % W/V |
|---|---|
| Tris | 0.1-0.5 |
| Sodium Phosphate, monobasic, monohydrate | 0.1-0.5 |
| Potassium Chloride | 0.01-0.5 |
| Mannitol | 4.0 |
| L-Carnitine | 0.1 |
| HPMC | 1.5 |
| Chondroitin sulfate | 0.5-5.0 |

Example 7

A viscoelastic composition is made by mixing the following components in the respective amounts listed in Table 7 at amounts per weight.

TABLE 7

| Component | % W/V |
|---|---|
| Tris | 0.1-0.5 |
| Sodium Phosphate, monobasic, monohydrate | 0.1-0.5 |
| Potassium Chloride | 0.01-0.5 |
| Mannitol | 4.0 |
| Erythritol | 0.1-0.5 |
| HPMC | 1.0 |
| Pluronic F127 | 5.0-20.0 |

Example 8

A viscoelastic composition is made by mixing the following components in the respective amounts listed in Table 8 at amounts per weight.

TABLE 8

| Component | % W/V |
|---|---|
| Tris | 0.1-0.5 |
| Sodium Phosphate, monobasic, monohydrate | 0.1-0.5 |
| Potassium Chloride | 0.01-0.5 |
| Mannitol | 4.0 |
| Erythritol | 0.1-0.5 |
| Chitosan | 1.0 |
| Pluronic F127 | 5.0-20.0 |

Example 9

A viscoelastic composition is made by mixing the following components in the respective amounts listed in Table 9 at amounts per weight.

TABLE 9

| Component | % W/V |
|---|---|
| Tris | 0.1-0.5 |
| Sodium Phosphate, monobasic, monohydrate | 0.1-0.5 |
| Potassium Chloride | 0.01-0.5 |
| Sorbitol | 4.0 |
| Xylitol | 1.0 |
| Aloe Vera | 2.0 |
| Pluronic F127 | 5.0-20.0 |

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the features and advantages appended hereto.

What is claimed is:

1. A viscoelastic composition comprising:
   (a) about 0.001 to about 1 wt. %, based on the total weight of the viscoelastic composition, of tris(hydroxymethyl)aminomethane or a salt thereof;
   (b) about 0.001 to about 2 wt. %, based on the total weight of the viscoelastic composition, of a phosphate buffer agent, wherein the phosphate buffer agent comprises one or more of sodium hydrogen phosphate monobasic, sodium hydrogen phosphate dibasic, potassium hydrogen phosphate monobasic and potassium hydrogen phosphate dibasic; and
   (c) about 0.001 to about 10 wt. %, based on the total weight of the viscoelastic composition, of a viscoelastic agent having an average molecular weight of about 500,000 to about 5,000,000;
   wherein the viscoelastic composition is one of a dispersive viscoelastic composition and a cohesive viscoelastic composition, the dispersive viscoelastic composition having a low-shear viscosity from about 20,000 centipoise (cPs) to about 80,000 cPs, and the cohesive viscoelastic composition having a low-shear viscosity of from about 75,000 cPs to about 475,000 cPs; and
   wherein the viscoelastic composition has a pH of about 6 to 7.8.

2. The viscoelastic composition of claim 1, comprising:
about 0.1 to about 0.5 wt. %, based on the total weight of the viscoelastic composition, of the tris(hydroxymethyl)aminomethane or the salt thereof;
about 0.1 to about 0.5 wt. %, based on the total weight of the viscoelastic composition, of the phosphate buffer agent; and
about 0.5 to about 5 wt. %, based on the total weight of the viscoelastic composition, of the viscoelastic agent.

3. The viscoelastic composition of claim 1, wherein the viscoelastic agent has an average molecular weight of about 500,000 to about 1,900,000.

4. The viscoelastic composition of claim 1, wherein the viscoelastic agent has an average molecular weight of about 2,000,000 to about 5,000,000.

5. The viscoelastic composition of claim 1, wherein the viscoelastic agent comprises a polysaccharide.

6. The viscoelastic composition of claim 5, wherein the polysaccharide comprises an anionic polysaccharide or a non-ionic polysaccharide.

7. The viscoelastic composition of claim 5, wherein the polysaccharide comprises one or more of hyaluronic acid or a salt thereof, chondroitin sulfate, chitosan, aloe vera, carboxymethylcellulose, hemicellulose, hydroxypropyl methyl cellulose, methylcellulose, and ethylcellulose.

8. The viscoelastic composition of claim 1, wherein the viscoelastic agent comprises one or more of hyaluronic acid, sodium hyaluronate, and potassium hyaluronate.

9. The viscoelastic composition of claim 1, further comprising one or more additives selected from the group consisting of an antioxidant, a non-ionic surfactant, an osmolyte and mixtures thereof.

10. The viscoelastic composition of claim 1, further comprising one or more additives selected from the group consisting of L-Carnitine, erythritol, and vitamin E TPGS (tocopheryl polyethylene glycol succinate).

11. The viscoelastic composition of claim 1, further comprising one or more additives selected from the group consisting of a poloxamer di(meth)acrylate, a reverse poloxamer di(meth)acrylate, a poloxamine di(meth)acrylate, and a reverse poloxamine di(meth)acrylate.

12. The viscoelastic composition of claim 1, further comprising one or more additives selected from the group consisting of NaCl, KCl; taurine, glycine, diglycine, alanine; mannitol, sorbitol and propylene glycol.

13. The viscoelastic composition of claim 1, having a pH of about 5.5 to 7.8.

14. The viscoelastic composition of claim 1, having a pH of about 7 to 7.8.

15. The viscoelastic composition of claim 1, wherein the pH of the viscoelastic composition is substantially the same at 22° C. and at 4° C.

16. The viscoelastic composition of claim 1, wherein the viscoelastic agent is hyaluronic acid or a salt thereof having an average molecular weight of about 500,000 to about 1,900,000.

17. A viscoelastic composition comprising:
(a) about 0.1 to about 0.5 wt. %, based on the total weight of the viscoelastic composition, of tris(hydroxymethyl) aminomethane or a salt thereof;
(b) about 0.1 to about 0.5 wt. %, based on the total weight of the viscoelastic composition, of a phosphate buffer agent, wherein the phosphate buffer agent comprises one or more of sodium hydrogen phosphate monobasic, sodium hydrogen phosphate dibasic, potassium hydrogen phosphate monobasic and potassium hydrogen phosphate dibasic; and
(c) about 0.5 to about 5 wt. %, based on the total weight of the viscoelastic composition, of hyaluronic acid or a salt thereof having an average molecular weight of about 500,000 to about 1,900,000;
wherein the viscoelastic composition is a dispersive viscoelastic composition having a low-shear viscosity from about 20,000 centipoise (cPs) to about 80,000 cPs; and
wherein the viscoelastic composition maintains a pH of about 6 to 7.8 at storage temperature and at room temperature during ocular surgery, the storage temperature being a temperature lower than room temperature.

18. The viscoelastic composition of claim 17, which maintains a pH of about 6.5 to 7.8, and wherein room temperature is at 22° C. and the storage temperature is at 4° C.

19. The viscoelastic composition of claim 17, which maintains a pH of about 7 to 7.8, and wherein room temperature is at 22° C. and the storage temperature is at 4° C.

20. The viscoelastic composition of claim 17, further comprising one or more additives selected from the group consisting of an antioxidant, a non-ionic surfactant, an osmolyte and mixtures thereof.

21. The viscoelastic composition of claim 17, further comprising one or more additives selected from the group consisting of L-Carnitine, erythritol, and vitamin E TPGS (tocopheryl polyethylene glycol succinate).

22. The viscoelastic composition of claim 17, further comprising one or more additives selected from the group consisting of NaCl, KCl; taurine, glycine, diglycine, alanine; mannitol, sorbitol and propylene glycol.

23. A viscoelastic composition comprising:
(a) about 0.1 to about 0.5 wt. %, based on the total weight of the viscoelastic composition, of tris(hydroxymethyl) aminomethane or a salt thereof;
(b) about 0.1 to about 0.5 wt. %, based on the total weight of the viscoelastic composition, of a phosphate buffer agent, wherein the phosphate buffer agent comprises one or more of sodium hydrogen phosphate monobasic, sodium hydrogen phosphate dibasic, potassium hydrogen phosphate monobasic and potassium hydrogen phosphate dibasic; and
(c) about 0.5 to about 5 wt. %, based on the total weight of the viscoelastic composition, of hyaluronic acid or a salt thereof having an average molecular weight of about 2,000,000 to about 5,000,000;
wherein the viscoelastic composition is a cohesive viscoelastic composition having a low-shear viscosity of from about 75,000 centipoise (cPs) to about 475,000 cPs; and
wherein the viscoelastic composition maintains a pH of about 6 to 7.8 at storage temperature and at room temperature during ocular surgery, the storage temperature being a temperature lower than room temperature.

24. The viscoelastic composition of claim 23, which maintains a pH of about 6.5 to 7.8, and wherein room temperature is at 22° C. and the storage temperature is at 4° C.

25. The viscoelastic composition of claim 23, which maintains a pH of about 7 to 7.8, and wherein room temperature is at 22° C. and the storage temperature is at 4° C.

26. The viscoelastic composition of claim 23, further comprising one or more additives selected from the group consisting of an antioxidant, a non-ionic surfactant, an osmolyte and mixtures thereof.

27. The viscoelastic composition of claim 23, further comprising one or more additives selected from the group consisting of L-Carnitine, erythritol, and vitamin E TPGS (tocopheryl polyethylene glycol succinate).

28. The viscoelastic composition of claim 23, further comprising one or more additives selected from the group consisting of NaCl, KCl; taurine, glycine, diglycine, alanine; mannitol, sorbitol and propylene glycol.

29. The viscoelastic composition of claim 1, wherein the viscoelastic composition maintains a pH of about 6 to 7.8 at storage temperature and at room temperature during ocular surgery, the storage temperature being a temperature lower than room temperature.

* * * * *